United States Patent
Camargo et al.

(10) Patent No.: US 12,181,342 B2
(45) Date of Patent: Dec. 31, 2024

(54) HEAT AND VOLATILE-ORGANIC-COMPOUNDS DETECTING SYSTEMS

(71) Applicant: Lam Research Corporation, Fremont, CA (US)

(72) Inventors: Francisco Jose Camargo, Tigard, OR (US); Jonathan Ross Angell, Gresham, OR (US)

(73) Assignee: Lam Research Corporation, Fremont, CA (US)

( * ) Notice: Subject to any disclaimer, the term of this patent is extended or adjusted under 35 U.S.C. 154(b) by 279 days.

(21) Appl. No.: 17/765,411

(22) PCT Filed: Oct. 20, 2020

(86) PCT No.: PCT/US2020/056526
§ 371 (c)(1),
(2) Date: Mar. 30, 2022

(87) PCT Pub. No.: WO2021/081000
PCT Pub. Date: Apr. 29, 2021

(65) Prior Publication Data
US 2022/0333995 A1   Oct. 20, 2022

Related U.S. Application Data

(60) Provisional application No. 62/926,289, filed on Oct. 25, 2019.

(51) Int. Cl.
*G01J 5/08* (2022.01)
*G01J 5/00* (2022.01)
(Continued)

(52) U.S. Cl.
CPC ........... *G01J 5/0853* (2013.01); *G01J 5/0096* (2013.01); *G01K 1/026* (2013.01); *G01N 33/0047* (2013.01)

(58) Field of Classification Search
CPC ........ G01J 5/0853; G01J 5/0096; G01J 5/025; G01J 5/046; G01J 5/0887; G01J 5/12;
(Continued)

(56) References Cited

U.S. PATENT DOCUMENTS 5,372,426 A   12/1994  Broudy et al.
5,716,133 A   2/1998   Hosokawa et al.

FOREIGN PATENT DOCUMENTS

CN   102822649 A   12/2012
CN   107659616 A   2/2018
(Continued)

OTHER PUBLICATIONS

International Application Serial No. PCT/US2020/056526, International Search Report mailed Feb. 15, 2021, 4 pgs.
(Continued)

*Primary Examiner* — Kiho Kim
(74) *Attorney, Agent, or Firm* — Schwegman Lundberg & Woessner, P.A.

(57) ABSTRACT

Various embodiments include heat and volatile-organic-compounds detecting systems. In one example, the heat-detecting system includes at least one heat sensor mounted externally to a device, such as a local power-box (LPB). The heat sensor has an area-of-detection to detect heat emitted from at least one face of the LPB at one or more locations. The heat-detecting system also includes a high-absorptance infrared-collector (HAIC) formed within the LPB to collect excessive heat generated by a component within the LPB. The excessive heat is correlated to a pre-determined temperature level, and a temperature of the collected excessive heat is measured by the heat sensor. Each of the heat sensor and the HAIC are coupled to a control module. Other apparatuses, designs, and methods are disclosed.

4 Claims, 9 Drawing Sheets

(51) Int. Cl.
*G01K 1/02* (2021.01)
*G01N 33/00* (2006.01)

(58) Field of Classification Search
CPC .. G01J 5/20; G01K 1/026; G01K 7/02; G01K 7/16; G01N 33/0047; G01N 1/24; G01N 2001/245; G01N 33/0036
See application file for complete search history.

(56) References Cited

FOREIGN PATENT DOCUMENTS

| | | |
|---|---|---|
| JP | S6323734 B2 | 5/1988 |
| JP | 6183637 B2 * | 8/2017 |
| JP | 2022552846 | 12/2022 |

OTHER PUBLICATIONS

International Application Serial No. PCT/US2020/056526, Written Opinion mailed Feb. 15, 2021, 6 pgs.
"International Application Serial No. PCT US2020 056526, International Preliminary Report on Patentability mailed May 5, 2022", 8 pgs.

* cited by examiner

HEAT AND VOLATILE-ORGANIC-COMPOUNDS DETECTING SYSTEMS

CLAIM OF PRIORITY

This application is a U.S. National Stage Filing under 35 U.S.C. 371 from International Application No. PCT/US2020/056526, filed on Oct. 20, 2020, and published as WO 2021/081000 A1 on Apr. 29, 2021, which claims the priority benefit to U.S. Patent Application Ser. No. 62/926,289, filed on 25 Oct. 2019, and entitled "HEAT AND VOLATILE-ORGANIC-COMPOUNDS DETECTING SYSTEMS," each of which is incorporated by reference herein in its entirety.

TECHNOLOGY FIELD

The disclosed subject matter is generally related to the field of detecting elevated temperatures within or near a localized volume, such as within a partially-enclosed or fully-enclosed container.

In a specific example, the disclosed subject matter relates to detecting elevated temperatures in and near environments such as local power-boxes (LPBs) used to supply high-voltage power to various pieces of equipment and tools, such as machining tools, heating and refrigeration equipment, semiconductor tools (e.g., metrology tools and processing tools), and a variety of other types of equipment and tools. More specifically, in various embodiments, the disclosed subject matter is related to automated detection of at least one of the detection of elevated temperatures through the use of various sensors and the detection of heat-generated volatile-organic-compounds (VOCs) emitted within the containers and power boxes.

BACKGROUND

Numerous types of tools and equipment have components that may overheat due to a variety of problems including improper component selection, improper connection of components, improper use of the tool or equipment, or even through failure or degradation of components with age. Overheating of components can cause substantial damage to the tool or equipment as well as work pieces or products being formed or manufactured within the equipment.

For example, many pieces of equipment rely on local power-boxes (LPB) and other devices to provide a supply of various voltages to components within the equipment. In the semiconductor industry for example, various semiconductor process-tools have one or more power boxes proximate to the tools to supply a range of voltages. There are often 400 connections within a power box. For various semiconductor process-tool manufacturers, thousands or even tens of thousands of power boxes are shipped annually, potentially resulting in up to several million chances each year for one of the connections within the LPB or device to fail. A failed connection can mean smoked, burned, and/or melted components at facilities in which these tools are located. The failed component can impact both the trust of the customer that purchased the tool as well as the productivity of each customer. Overall, a typical cost of a failed component can result in tens of thousands of dollars or even hundreds of thousands of dollars (as measured in USD) per incident. In addition to new tools shipped that are coupled with one or more LPBs each year, hundreds of new connections are made or reworked each year during an LPB retrofit or upgrade, resulting in an additional added risk.

Elevated temperatures within LPBs and other devices can be caused by a number of problems such as, an improper torque on wiring connectors, improper crimping techniques (both over and under crimping) on wiring connectors, one or more improper gauges of wire used in the original construction of the LPB or device, and other factors understood by a person of ordinary skill in the art. Typical initial testing of LPBs and other devices includes infrared (IR) inspection techniques, which can catch some but not all problems listed above since, for example, (1) some issues develop over time and at variable load conditions; (2) LPB and other device testing is not necessarily performed at full load conditions; and (3) LPB and device testing is not performed continuously during operation of the tool. Therefore, contemporaneous testing techniques are estimated as only being approximately 67% effective. Even so, current testing techniques rely on repeat testing of tools in the field at, for example, six-month intervals. Therefore, a more effective means of detecting elevated temperatures within LPBs and other devices, in substantially real-time, is needed.

The background description provided here is for the purpose of generally presenting the context of the disclosed subject matter. Work of the presently named inventors, to the extent that it is described in this background section, as well as aspects of the description that may not otherwise qualify as prior art at the time of filing, are neither expressly nor impliedly admitted as prior art against the present disclosure. Consequently, the information described in this section is provided to offer the skilled artisan a context for the following disclosed subject matter and should not be considered as admitted prior art. The information described in this section is therefore provided to offer the skilled artisan a context for the following disclosed subject matter and should not be considered as admitted prior art.

SUMMARY

An embodiment of the disclosed subject matter describes a heat-detection system having at least one heat sensor mounted externally to a local power-box (LPB). The heat sensor has an area-of-detection to detect heat emitted from at least one face of the LPB at one or more locations. A high-absorptance, infrared-collector (HAIC) formed within the LPB is arranged to collect excessive heat generated by a component within the LPB. The excessive heat is correlated to a pre-determined temperature level. A temperature of the collected excessive heat to be measured by the at least one heat sensor. The heat sensors and the HAIC are coupled to a control module.

An embodiment of the disclosed subject matter describes a heat-detection system including at least one volatile-organic-compound (VOC) sensor mounted within a device to detect reducing gases produced by outgassing as one or more components within the device approach their respective melting points. The at least one VOC sensor is coupled to a control module.

An embodiment of the disclosed subject matter describes a heat-detection system for a device. The system includes a number of heat sensors mounted within the device, with each of the heat sensors having an area-of-detection to detect heat emitted from at least one of a plurality of components mounted within the device. A control module is in electrical communication with the number of heat sensors; the control module is arranged to collect electrical signals from the plurality of components where a level of the electrical signals corresponds to a level of temperature. The control module is further arranged to make a determination when at least one of the electrical signals received from the plurality of components exceeds a corresponding pre-determined temperature level.

An embodiment of the disclosed subject matter describes a heat-detection system to detect heat generated by a device. The system includes at least one rope comprised of a plurality of thermocouples that traverses areas within the device; each of the ropes are arranges to detect heat emitted from at least one of a plurality of components mounted within the device. A control module is in electrical communication with the at least one rope. The control module is arranged to collect electrical signals from the plurality of thermocouples within the at least one rope where a level of the electrical signals corresponds to a level of temperature. The control module is further arranged to make a determination when at least one of the electrical signals received from the plurality of components exceeds a corresponding pre-determined temperature level.

An embodiment of the disclosed subject matter describes a heat-detection system to detect heat generated by a device. The system includes at least one linear heat-detection cable placed within the device to detect heat generated in a device. The at least one linear heat-detection cable having a polymer-based thermally reactive sheathing to detect heat emitted from at least one of a plurality of components mounted within the device to detect heat generated by at least one of the plurality of components. A control module is in electrical communication with the at least one linear heat-detection cable with the control module being arranged to collect electrical signals from the at least one linear heat-detection cable. A level of the electrical signals corresponds to a level of temperature. The control module is further arranged to make a determination when at least one of the electrical signals received from the plurality of components exceeds a corresponding pre-determined temperature level.

DETAILED DESCRIPTION

The description that follows includes illustrative examples, devices, and apparatuses that embody various aspects of the disclosed subject matter. In the following description, for purposes of explanation, numerous specific details are set forth in order to provide an understanding of various embodiments of the inventive subject matter. It will be evident however, to those of ordinary skill in the art, that various embodiments of the disclosed subject matter may be practiced without these specific details. Further, well-known structures, materials, and techniques have not been shown in detail, so as not to obscure the various illustrated embodiments.

Various exemplary embodiments discussed below focus on detecting elevated temperatures within various devices that contain components capable of producing excessive heat. A temperature related to "excessive heat" may be determined readily by a person of ordinary skill in the art based on the type of device in use. In one specific exemplary embodiment, the device may be one or more local power-boxes (LPBs) used to supply high-voltage power to equipment, although any limitation to LPBs only is not intended. Upon reading and understanding the disclosure provided herein, a person of ordinary skill in the art will readily understand that the various techniques, designs, and examples may all be applied singly or in various combinations. As an introduction to the subject, a few embodiments will be described briefly and generally in the following paragraphs, and then a more detailed description, with reference to the figures, will ensue.

Various ones of the exemplary embodiments described herein are arranged to detect elevated temperatures within a device or LPB in substantially real-time. The embodiments allow either continuous or periodic temperature-monitoring of the device or LPB to sense temperature spikes and escalating temperature during, for example, ramp-up and power-on cycles, as well during steady-state operations of a tool. Each of the various embodiments is arranged to either shut down a device or an LPB automatically and/or alert an end-user of a tool before a catastrophic failure can occur. Further, each of the various embodiments can be configured to allow continuous data logging of temperature trends within a device or an LPB. Moreover, as will be understood by a person of ordinary skill in the art upon reading and understanding the disclosed subject matter, one or more the various embodiments disclosed may be used in combination with one another.

Figure 1B:
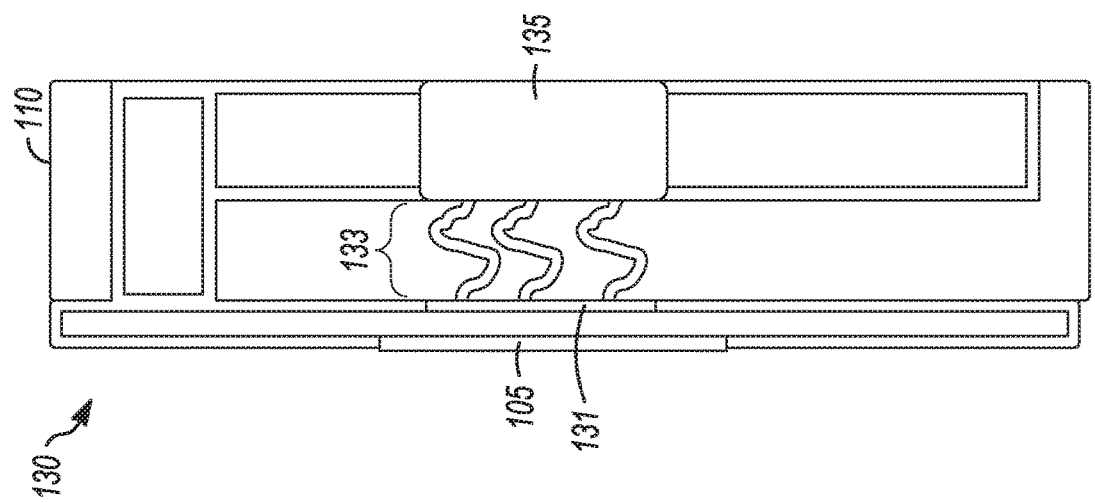
FIG. 1B shows an exemplary embodiment of a side-view of the LPB of FIG. 1A, and indicates a position of a failed component, as well as an HAIC placed on or above a front cover of the LPB.
Figure 1A:
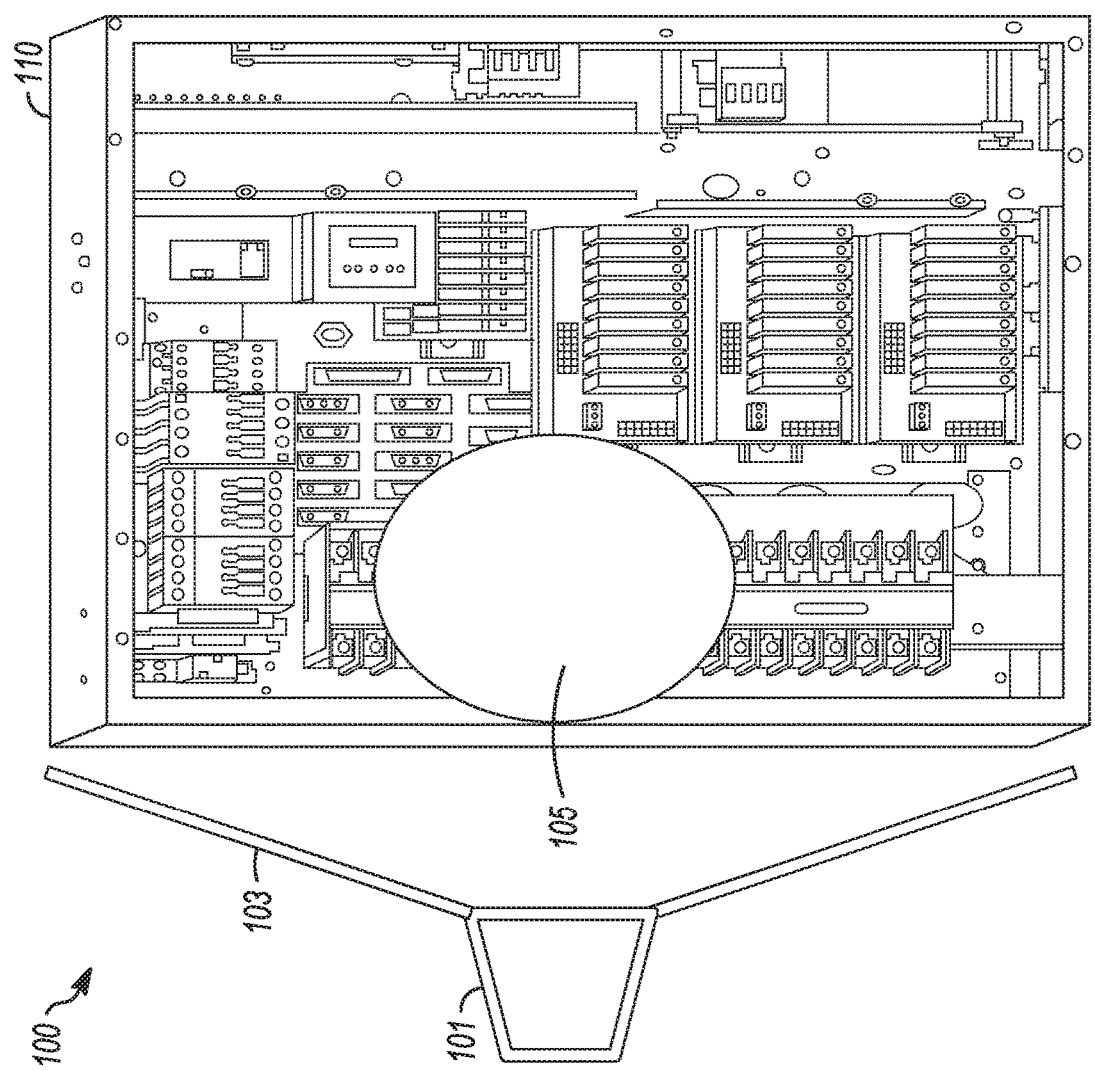
FIG. 1A shows an exemplary embodiment of a front-view of a local power-box (LPB, a front cover is not shown so as to avoid obscuring details of the disclosed subject matter) having a single heat-sensor, situated external to the LPB, to sense excessive heat generated within the LPB.

With reference now to FIG. 1A, an exemplary embodiment of a front-view 100 of a local power-box 110 (LPB, a front cover of the LPB is not shown so as to avoid obscuring details of the disclosed subject matter) having a single heat sensor 101, situated external to the LPB 110. As will be recognized by a person of ordinary skill in the art upon reading and understanding the disclosed subject matter, although various figures may refer to an LPB, such construction is provided for brevity only as the disclosed subject matter may be used with any device having components capable of generating heat and not necessarily only an LPB.

The heat sensor 101 is used to sense excessive heat on an external area 105 that is generated within the LPB 110. As shown, the heat sensor 101 may have an area-of-detection 103 sufficient to cover an entire area of one or more faces of the LPB 110 or may have a limited area, such as an area sufficient to cover the external area 105, as discussed in more detail below. Moreover, although only a single heat sensor 101 is shown for clarity, a person of ordinary skill in the art will understand that multiple heat sensors (of one or more types) may be used. The heat sensor 101 may comprise any type of heat sensor known in the relevant art such as, for example, an infra-red (IR)-based heat sensor.

FIG. 1B shows an exemplary embodiment of a side-view 130 of the LPB 110 of FIG. 1A, and indicates an example of a failed component 135, as well as a high-absorptance IR-collector (HAIC) 131 placed on or proximate to a front cover or other external surface of the LPB 110. Generated heat 133 from the failed component 135, which, in this example, has failed or may fail soon due to excessive heat being generated in or near the component, is collected by the HAIC 131. The heat collected by the HAIC 131 in turn radiates to the external area 105, thereby raising the local temperature of the external area 105. The heat sensor 101 then detects the elevated temperature of the external area 105.

The HAIC 131 is formed over at least a portion of the LPB 110. The heat sensor 101 may, in some embodiments, be positioned in proximity to one or more locations in which the HAIC 131 is formed. Also, the area-of-detection 103 of the heat sensor 101 may be limited to cover substantially only an area in which each of the one or more HAICs 131 are located. For example, the HAIC 131 may be formed on an inside face of the front cover (not shown) of the LPB 110, an exterior wall of the LPB 110, or another area that may be monitored readily by the heat sensor 101.

The HAIC 131 collects the generated heat 133 (or residual heat) from suspected or anticipated generators of heat within the LPB 110. Once the generated heat 133 is collected, a temperature of the HAIC 131 increases and is readily detectable by the heat sensor 101. Since the heat sensor 101 is configured to be mounted permanently and proximate to the LPB 110, temperatures within the LPB 110 are monitored continuously. In other embodiments, temperatures within the LPB 110 may be monitored at predetermined intervals (e.g., only during ramp-up of the tool coupled to the LPB 110, during anticipated peak-load demands on the tool, etc.).

With continuous reference now to both FIGS. 1A and 1B, the HAIC 131 may comprise a coating material having a high level of thermal absorptance, coupled with a low level of reflectance. Such materials are known in the art and are used in fabricating, for example, thermal solar collectors. In a specific exemplary embodiment, the HAIC 131 is a MaxiBlack™ black-film coating (manufactured by Acktar Ltd., 19 Topaz St., POB 8643; Kiryat-Gat, 8213513 Israel). MaxiBlack™ is a graphene-based black-film polymer film that can be applied (e.g., with an available applied-adhesive layer) to various surfaces. The graphene absorbs radiant energy (e.g., IR energy from heated components) to heat the graphene-based film to, for example, 160° C. in a few seconds. The heat sensor 101 will therefore sense the absorbed heat from the HAIC 131 quickly. In other exemplary embodiments, the HAIC 131 may comprise another type of high-absorptance coating capable of absorbing radiant energy (e.g., IR energy) such as, for example, a high-absorptance paint or other material for the wavelengths (e.g., IR) of interest. The skilled artisan will recognize that the external area 105 and the HAIC 131 as shown in FIGS. 1A and 1B are for illustrative purposes only. The actual area may be larger or smaller, with reference to the LPB 110, than shown. Also, the HAIC 131 may be placed in a number of locations within or on the LPB 110.

If the heat sensor 101 determines that a temperature of the LPB 110 (e.g., as measured at the external area 105) has surpassed a pre-determined temperature (e.g., the pre-determined temperature being related to a safety level for both the LPB and an operator), the heat sensor 101 can be arranged to send an alert signal to a control unit (CU, not shown), located with the LPB 110, on the tool, or at a remote location. The CU can be pre-programmed to take certain preventive actions, such as shutting down power being delivered to the LPB 110 or alerting an operator of the tool that an internal temperature level of the LPB 110 has been exceeded. The operator may then perform appropriate actions to safely shut down the LPB 110.

Figure 2:
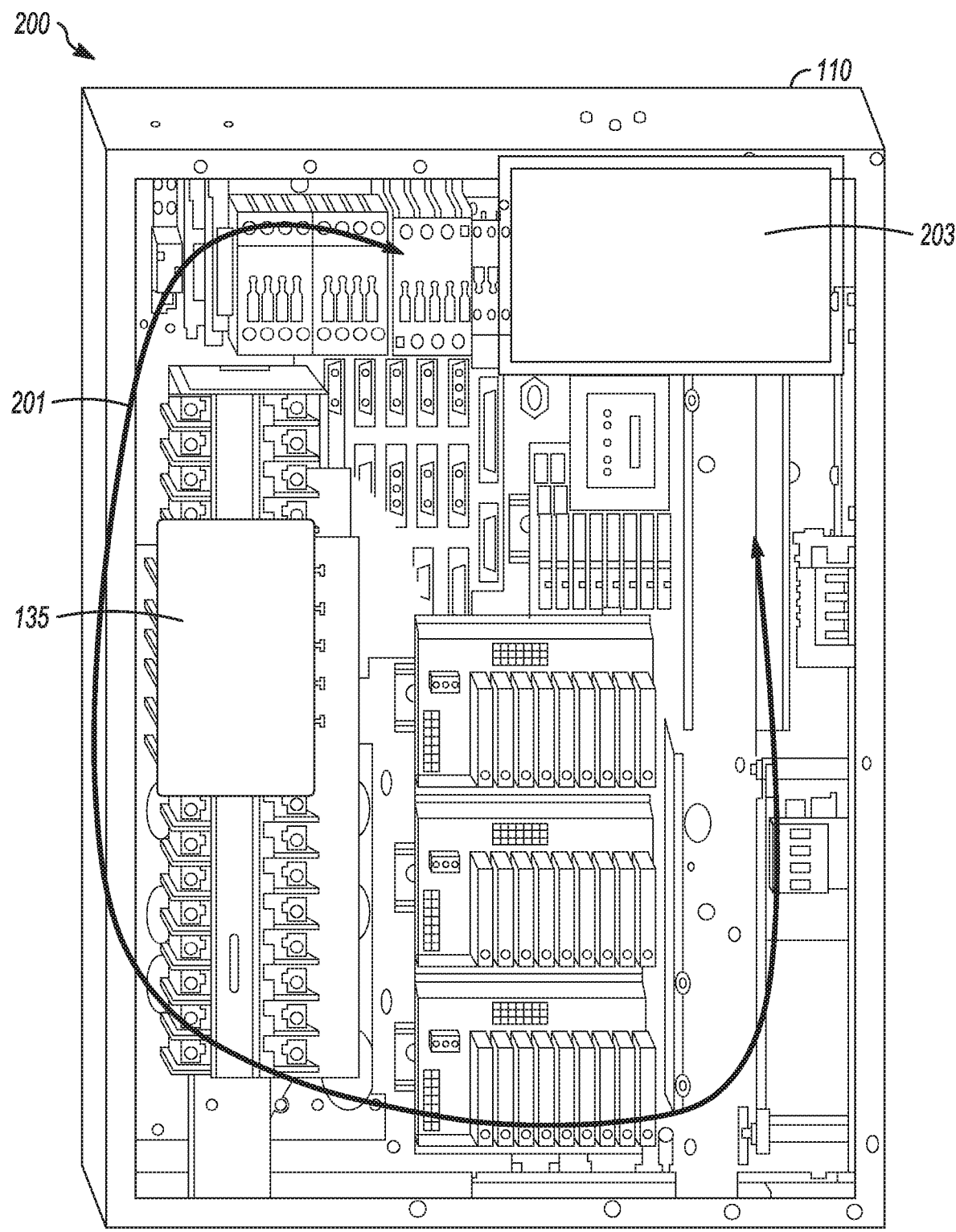
FIG. 2 shows an internal view of an LPB having a volatile-organic-compound (VOC) sensor.

FIG. 2 shows an internal view of an LPB having a volatile-organic-compound (VOC) sensor 203. The VOC sensor 203 is known in the art and is configured to sense and measure ambient concentrations of a broad range of reducing gases formed within the LPB 110. Such reducing gases are produced during outgassing as the parts or components within the LPB 110 are at or approaching their respective melting points. The reducing gases may comprise, for example, amines, organic chloramines, aliphatic and aromatic hydrocarbons, as well as other gases produced by heated or melting components (e.g., nylons, plastics, etc.) used as dielectric materials in manufacturing LPBs. Although only a single VOC sensor 203 is shown, no such limitation is intended. A person of ordinary skill in the art will recognize that more than one VOC sensor 203 may be included within the LPB 110. For example, two or more VOC sensors 203 may be used to reduce or minimize false alarms. In another example, two or more VOC sensors 203 may be used with one VOC sensor 203 used at a fresh-air inlet to the LPB 110 with the second VOC sensor 203 being placed within the LPB 110 as shown. The VOC sensor 203 placed at the inlet can serve as a baseline sensor for VOCs. In this example, the inlet VOC sensor can provide a baseline, such as when technicians are using alcohol to clean components outside the LPB 110. The inlet VOC can then be arranged to prevent the second VOC sensor from triggering an alarm if the relative amount of VOCs measured by each VOC sensor is the same or close to being the same within a predetermined level.

FIG. 2 also shows a convection current 201 that is produced by fans mounted on or in the LPB 110. Additionally, in various embodiments, one or more small fans (not shown) may be added within the LPB 110 to further circulate air (for example, from the failed component 135 to the VOC sensor 203) within the LPB 110. Air circulated by convection current 201 within the LPB 110 is therefore detected more readily by the VOC sensor 203.

Consequently, in one embodiment, the VOC sensor 203 can be arranged to continuously monitor outgassing of parts that are at or approaching their respective melting points. In another embodiment, the VOC sensor 203 can be arranged to periodically monitor (e.g., as noted with reference to the heat sensor 101 of FIG. 1A) outgassing of parts that are at or approaching their respective melting points. If the VOC sensor 203 determines that a concentration of volatile compounds has surpassed a pre-determined level (e.g., a pre-determined safety level), the VOC sensor 203 can be arranged to send an alert signal to a control unit (CU) or control module (CM), located with the LPB 110, on the tool, or at a remote location. The CU or CM can be pre-programmed to take certain preventive actions, such as shutting down power being delivered to the LPB 110 or alerting an operator of the tool that an internal temperature level of the LPB 110 has been exceeded. The operator may then perform appropriate actions to safely shut down the LPB 110.

Upon reading and understanding the disclosed subject matter, a person of ordinary skill in the art will recognize that the embodiments described in FIGS. 1A, 1B, and 2 may be combined. In such a combination, the heat sensor 101 and the HAIC 131, forms a primary thermal-detection system and the VOC sensor 203 forms a secondary thermal-detection system, whereby both systems send their respective signals to the CU or CM. In other embodiments of this combination, signals received by the CU of CM from the VOC sensor 203 may be given priority over the heat sensor 101 and the HAIC 131. In still other embodiments of this combination, signals received by the CU or CM from either the heat sensor 101 and the HAIC 131 or from the VOC sensor 203 may be given equal priority—if the CU or CM receives a signal from either one of the systems, one or more preventive actions, as described above, may be performed.

Figure 3A:
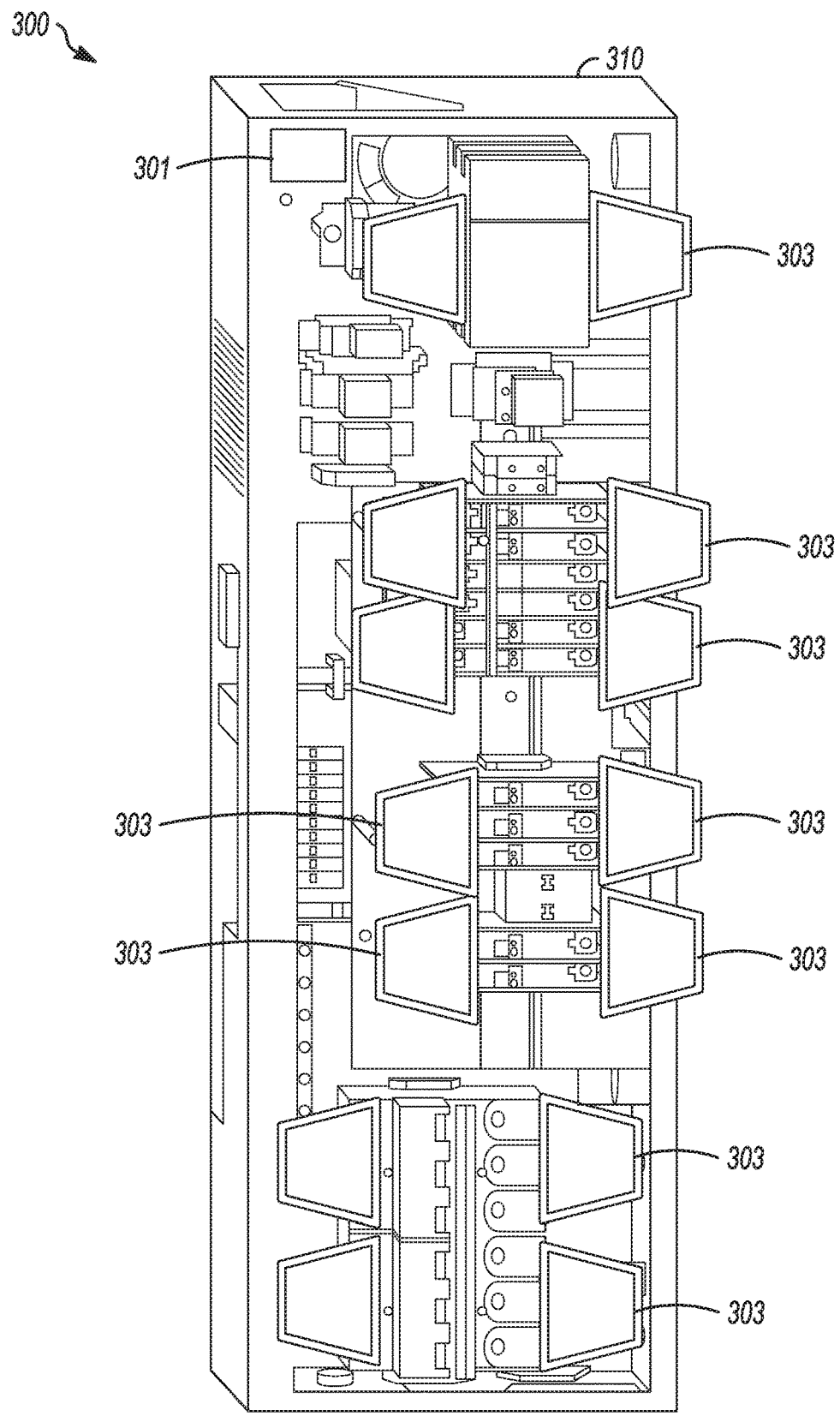
FIG. 3A shows an exemplary embodiment of an internal view of an LPB having a number of heat sensors placed therein.

FIG. 3A shows an exemplary embodiment of an internal view 300 of an LPB 310 (e.g., an upper LPB) having a number of heat sensors 303 placed therein. FIG. 3A is also shown to include a control module (CM) 301 located within the LPB 310. Various types and arrangements, as hardware-based, firmware-based, or software-based configurations, of the CM 301 are described in more detail, below.

Since individual ones of the heat sensors 303 may have a limited viewing-angle (typically about 90° to 100° for commercially available units), using a larger number of heat sensors 303 enables coverage of all or most components within the LPB 310. That is, the volume within an LPB 310 is limited. Therefore, increasing the number of heat sensors 303 allows for coverage of all or substantially all of the components within the LPB 310 since no one of the heat sensors 303 may be able to be mounted sufficiently far enough away to cover all, or even a majority of, the components with only a single or limited number of the heat sensors 303.

Each of the heat sensors 303 may comprise various types of thermal-detection instruments including, for example, a thermocouple, an infra-red sensor, or some other type of thermal-detection device (e.g., resistance temperature-detectors (RTDs)) known in the art. In various embodiments, the heat sensors may comprise on or more of the thermal-detection instruments. Each of the heat sensors 303 may be electrically coupled to the CM 301 within the LPB 310 or to a remote CU or CM outside of the LPB. Upon receiving a signal from one or more of the heat sensors 303 indicating that a pre-determined temperature level has been exceeded, the CM 301 or the remote CU or CM can be pre-programmed to take certain preventive actions, such as shutting down power being delivered to the LPB 310 or alerting an operator of the tool that an internal temperature level of the LPB 310 has been exceeded. The operator may then perform appropriate actions to safely shut down the LPB 310.

Figure 3B:
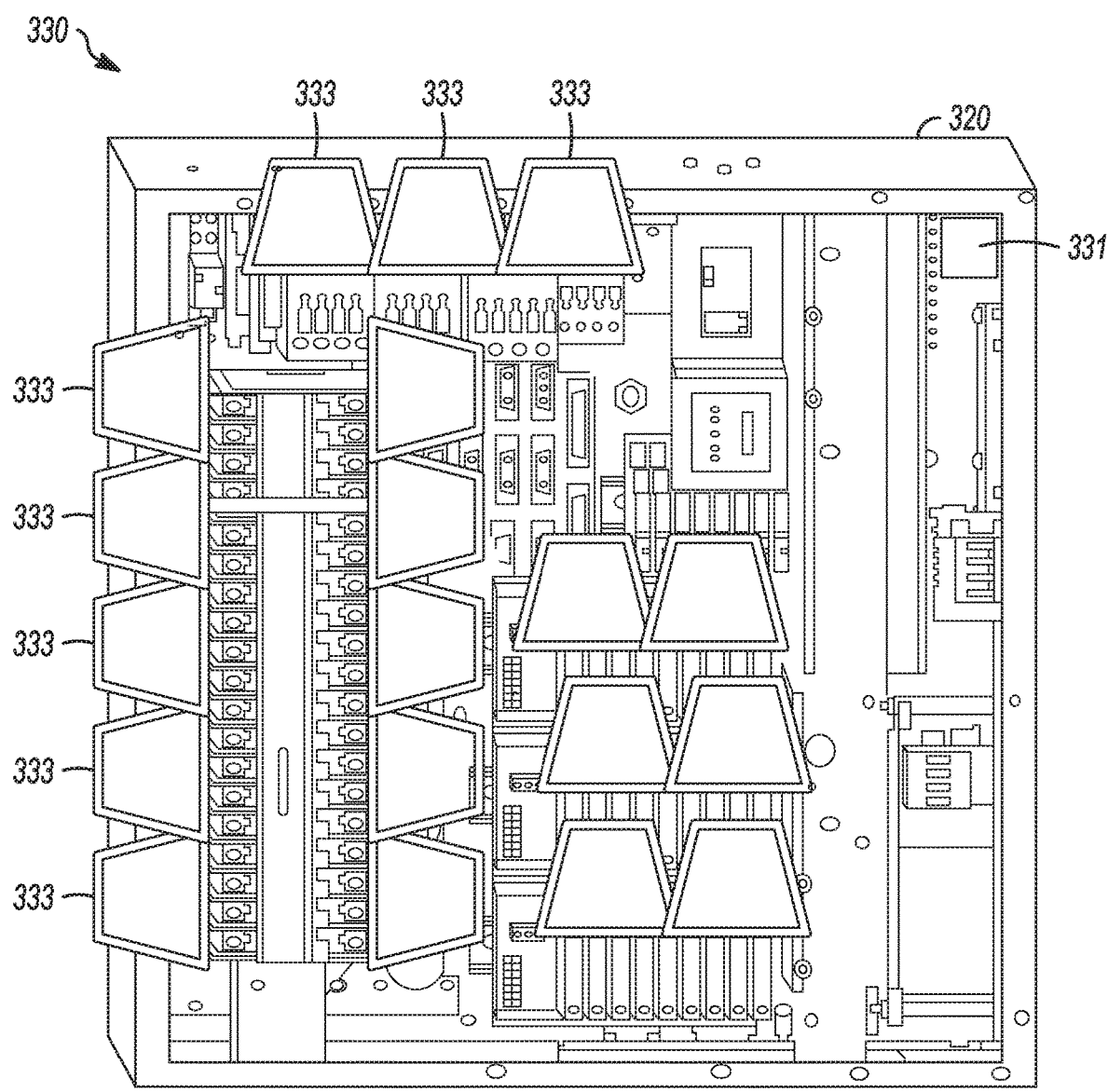
FIG. 3B shows another exemplary embodiment of an internal view of an LPB having a number of heat sensors placed therein.

FIG. 3B shows another exemplary embodiment of an internal view of an LPB 320 (e.g., a lower LPB box) having a number of heat sensors 333 placed therein. FIG. 3B is also shown to include a control module (CM) 331 located within the LPB 320. Each of the heat sensors 333 may be the same as or similar to the heat sensors 303 of FIG. 3A. Additionally, the CM 331 may be the same as or similar to the CM 301 of FIG. 3A. Each of the CM 301 and the CM 331 may be coupled to be in communication with a remote CU or CM outside of the respective LPB 310, 330. In either of the embodiments of FIG. 3A or 3B, a heat sensor (e.g., the same as or similar to the heat sensor 101 of FIG. 1A) may also be mounted externally to the respective LPBs 310, 320. In a specific exemplary embodiment, approximately 30 or more heat sensors 303, 333 may be used to provide sufficiently uniform coverage of the upper and lower power boxes (LPB 310 and LPB 330).

In various embodiments, the CM 301 of FIG. 3A and the CM 331 of FIG. 3B may electrically be coupled wirelessly to one another (e.g., by wireless operations including radio-frequency, Bluetooth®, and other protocols known in the relevant art) or hard-wired (e.g., physically wired directly or through various LAN protocols) to one another. Upon receiving a signal from one or more of the heat sensors 303 and/or the heat sensors 333 indicating that a pre-determined temperature level has been exceeded, one or more of the CM 301, the CM 331, and the remote CU or CM can be pre-programmed to take certain preventive actions, such as shutting down power being delivered to a respective one or both of the LPB 310, 330 or alerting an operator of the tool that an internal temperature level of the LPB 310, 330 has been exceeded. The operator may then perform appropriate actions to safely shut down one or both of the LPB 310, 330.

Figure 4A:
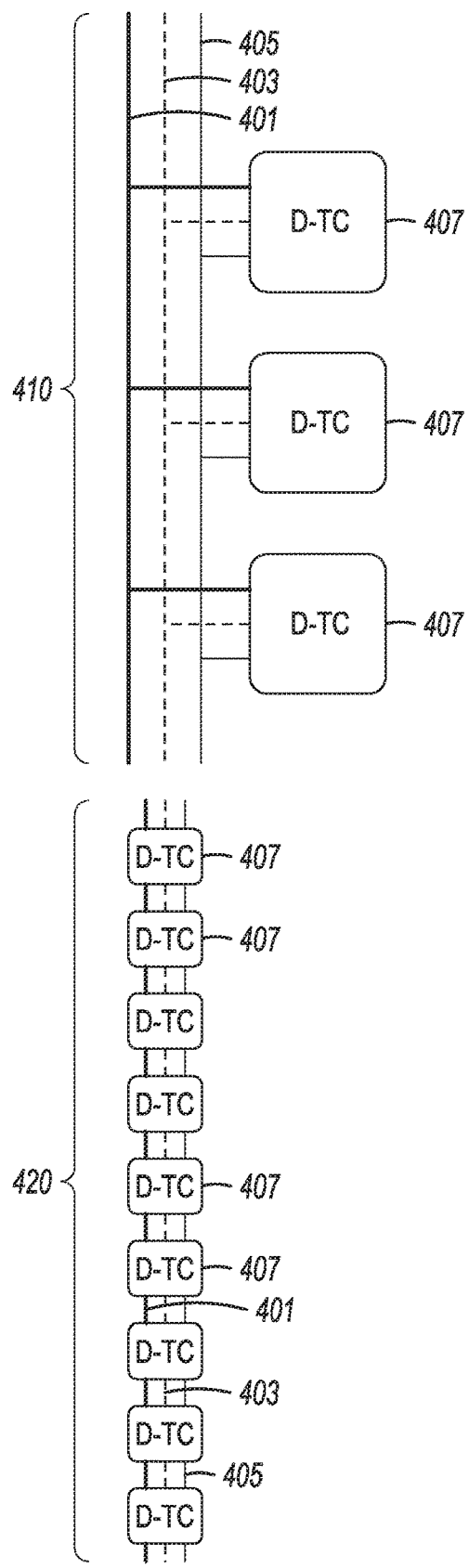
FIG. 4A shows an example of a string of digital thermocouples (D-TCs) for use within an LPB in accordance with various examples of the disclosed subject matter.

FIG. 4A shows an example of a string of digital thermo-couples (D-TCs) 410, 420 for use within an LPB in accordance with various examples of the disclosed subject matter. Each of the strings of D-TCs 410, 420 include a number of individual D-TCs 407 that are electrically coupled to each other through, for example, a $V_{CC}$ connection 401, a data connection 403, and a ground connection 405. In a specific exemplary embodiment, one of the strings of D-TCs 410, 420 that is approximately 1.22 meters (approximately 48 inches) may be run near various components within an LPB to cover all or substantially all of the components within the LPB. Such arrangements are described in more detail with reference to FIGS. 4B and 4C, below.

As shown in FIG. 4A, the string of D-TCs 410, 420 are arranged to electrically be coupled to each other in a parallel connection. However, at least portions of the string of D-TCs 410, 420 may be arranged to electrically be coupled in a series connection or in a hybrid series-parallel connection in limited areas of the string. For example, a large number of D-TCs 407 may be clustered in series near a particular component within an LPB such that if any one of the D-TCs 407 senses a temperature that has exceeded a pre-determined temperature level, a signal is sent to a CM as described below with reference to FIGS. 4B and 4C. Further, upon reading and understanding the disclosed subject matter, a person of ordinary skill in the art will recognize that one or more of the D-TCs 407 may be substituted or used in addition to other types of thermal-detection devices described herein (e.g., such as RTDs) as known in the relevant art.

Figure 4B:
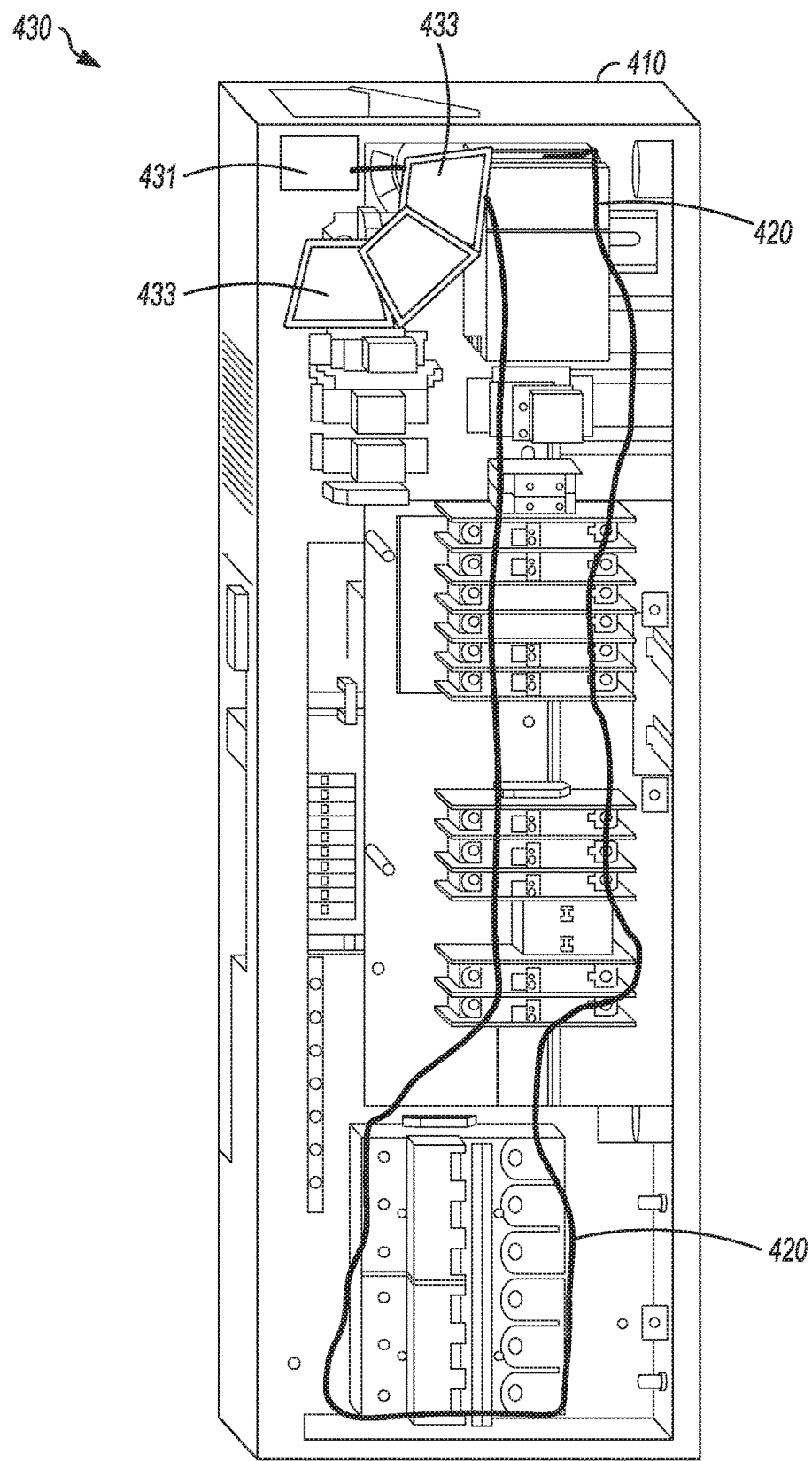
FIG. 4B shows an exemplary embodiment of the string of D-TCs of FIG. 4A, as well as a number of heat sensors, used within an LPB to detect excessive heat generated within the LPB.

Referring now to FIG. 4B, an exemplary embodiment 430 of the string of D-TCs 410, 420 of FIG. 4A, as well as a number of heat sensors 433, used within an LPB 410 (e.g., an upper LPB) to detect excessive heat generated within the LPB 410, are shown. FIG. 4B is also shown to include a control module (CM) 431 within the LPB 410. Each of the heat sensors 433 may be the same as or similar to the heat sensors 303 of FIG. 3A. Additionally, the CM 431 may be the same as or similar to the CM 301 of FIG. 3A. The CM 431 may also be coupled to a remote CU or CM outside of the LPB 410.

A rope 420 comprising the string of D-TCs 410, 420 of FIG. 4A, is shown to traverse various portions of the LPB 410. A skilled artisan will of course recognize various ones of the components within a given LPB under which the rope 420 should be run (e.g., high-power circuit breakers). In one example, the rope 420 may be run under or within a track used to mount various components within the LPB 410. Further, although only three heat sensors are shown, and all three of the heat sensors 433 are placed in close proximity to the CM 431, no such limitation is intended. More or fewer ones of the heat sensors 433 may be used in various locations within the LPB 410.

Additionally, the rope 420 may comprise a number of flexible or fixed printed-circuit boards (PCBs), all coupled to at least the CM 431, and potentially to one another, by various wireless or wired connections as described herein. Moreover, some or all of the PCBs can include another type of heat sensor (e.g., an RTD or IR sensor as described herein).

Each of the one or more ropes 420, or the D-TCs 407 coupled to the one or more ropes 420, as well as the heat sensors 433, may electrically be coupled to the CM 431 within the LPB 410 or to a remote CU or CM outside of the LPB. Upon receiving a signal from at least one of the one or more ropes 420, the DI-TCs 407, or the heat sensors 433, indicating that a pre-determined temperature level has been exceeded, the CM 431 and/or the remote CU or CM can be pre-programmed to take certain preventive actions, such as shutting down power being delivered to the LPB 410 or alerting an operator of the tool that an internal temperature level of the LPB 410 has been exceeded. The operator may then perform appropriate actions to safely shut down the LPB 410.

Figure 4C:
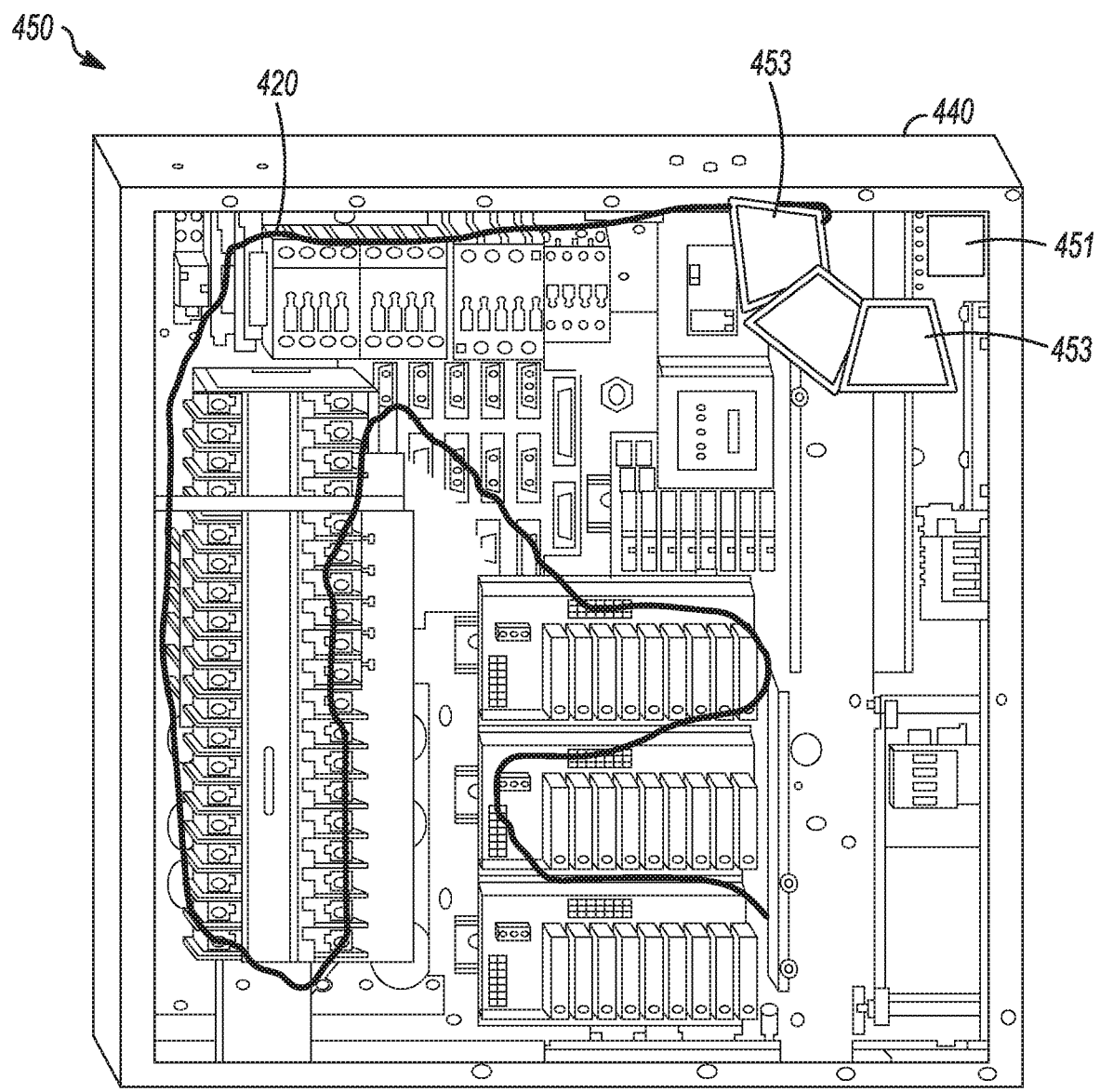
FIG. 4C shows another exemplary embodiment of the string of D-TCs of FIG. 4A, as well as a number of heat sensors, used within an LPB to detect excessive heat generated within the LPB.

FIG. 4C shows another exemplary embodiment 450 of the string of D-TCs 410, 420 of FIG. 4A, as well as a number of heat sensors 453, used within an LPB 440 (e.g., a lower LPB box) to detect excessive heat generated within the LPB 440. Each of the heat sensors 453 may be the same as or similar to the heat sensors 303 of FIG. 3A. Additionally, the CM 451 may be the same as or similar to the CM 301 of FIG. 3A. Each of the CM 431 (of FIG. 4B) and the CM 451 may be coupled to a remote CU or CM outside of the respective LPB 410, 440.

A rope 420 comprising the string of D-TCs 410, 420 of FIG. 4A, is shown to traverse various portions of the LPB 440. A skilled artisan will of course recognize various ones of the components within a given LPB under which the rope 420 should be run. As described with reference to FIG. 4B, in one example, the rope 420 may be run under or within a track used to mount various components within the LPB 440. Further, although only three heat sensors are shown, and all three of the heat sensors 453 are placed in close proximity to the CM 451, no such limitation is intended. More or fewer ones of the heat sensors 453 may be used in various locations within the LPB 440.

Additionally, the rope 420 may comprise a number of flexible or fixed printed-circuit boards, all coupled to at least the CM 451, and potentially to one another, by various wireless or wired connections as described herein. Moreover, some or all of the PCBs can include another type of heat sensor (e.g., an RTD or IR sensor as described herein). Each of the one or more ropes 420, or the DI-TCs 407 coupled to the one or more ropes 420, as well as the heat sensors 453, may be coupled electrically to the CM 451 within the LPB 440 or to a remote CU or CM outside of the LPB.

In either of the embodiments 430, 450 of FIG. 4B or FIG. 4C, the rope 420 could also be attached or thermally coupled to a panel behind one or more components (e.g., breakers) within the respective LPB 410, 440 or on an internal portion of a front panel covering the respective LPB 410, 440. For example, in a specific exemplary embodiment, the rope 420 could be adhered chemically (e.g., by an adhesive), by double-sided tape, or otherwise mechanically fastened (e.g., tie mounts) to appropriate portions of the respective LPB 410, 440. In either of the embodiments of FIG. 4B or 4C, a heat sensor (e.g., the same as or similar to the heat sensor 101 of FIG. 1A) may also be mounted externally to the respective LPBs 410, 440.

In various embodiments, the CM 431 of FIG. 4B and the CM 451 of FIG. 4C may electrically be coupled wirelessly to one another (e.g., by wireless operations including radio-frequency, Bluetooth®, and other protocols known in the relevant art) or hard-wired (e.g., physically wired directly or through various LAN protocols) to one another. Upon receiving a signal from at least one of the one or more ropes 420, the D-TCs 407, or the heat sensors 433, 453 indicating that a pre-determined temperature level has been exceeded, one or more of the CM 431, the CM 451, and the remote CU or CM can be pre-programmed to take certain preventive actions, such as shutting down power being delivered to a respective one or both of the LPB 410, 440 or alerting an operator of the tool that an internal temperature level of the LPB 410, 440 has been exceeded. The operator may then perform appropriate actions to safely shut down one or both of the LPBs 410, 440.

Figure 5A:
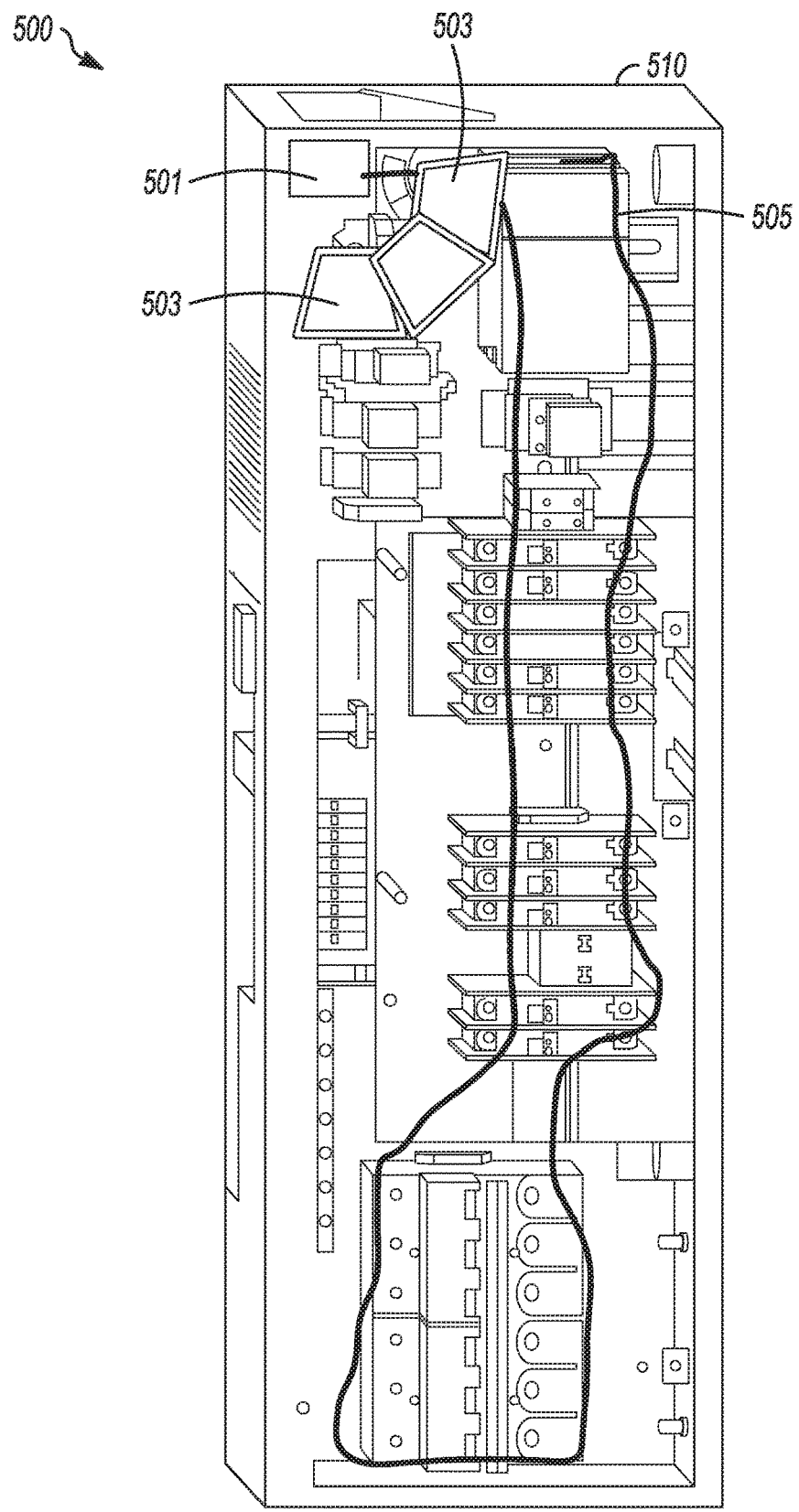
FIG. 5A shows an exemplary embodiment of a linear heat-detection (LHD) cable, as well as a number of heat sensors, used within an LPB to detect excessive heat generated within the LPB.

Referring now to FIG. 5A, FIG. 5A shows an exemplary embodiment 500 of a linear heat-detection (LHD) cable 505, as well as a number of heat sensors 503, used within an LPB 510 (e.g., an upper LPB) to detect excessive heat generated within the LPB 510. FIG. 5A is also shown to include a control module (CM) 501 located within the LPB 510. Each of the heat sensors 503 may be the same as or similar to the heat sensors 303 of FIG. 3A. Additionally, the CM 501 may be the same as or similar to the CM 301 of FIG. 3A. In various embodiments, the CM 501 may also be coupled to a remote CU or CM outside of the LPB 510.

In a specific exemplary embodiment, the LHD cable 505 comprises a linear-heat cable known as Protectowire® (manufactured by Fike® Corporation, 704 SW Tenth Street, Blue Springs, Missouri, USA 64015). Protectowire® comprises a continuous run of spot-based heat detectors that includes a tri-metallic core (providing tensile strength for the cable as well as electrical conductivity) having a heat-sensitive, polymer-based thermally reactive sheathing surrounding the metallic core. An outer diameter of the cable is about 3.18 mm (approximately ⅛ inch).

In various embodiments, the heat sensors 503 and the LHD cable 505 are coupled to the CM 501 and/or the remote CU or CM outside the LPB 510. Upon receiving a signal from one or more of the heat sensors 503 and/or the LHD cable 505 indicating that a pre-determined temperature level has been exceeded, one or more of the CM 501 and the remote CU or CM can be pre-programmed to take certain preventive actions, such as shutting down power being delivered to the LPB 510 or alerting an operator of the tool that an internal temperature level of the LPB 510 has been exceeded. The operator may then perform appropriate actions to safely shut down the LPB 510.

Figure 5B:
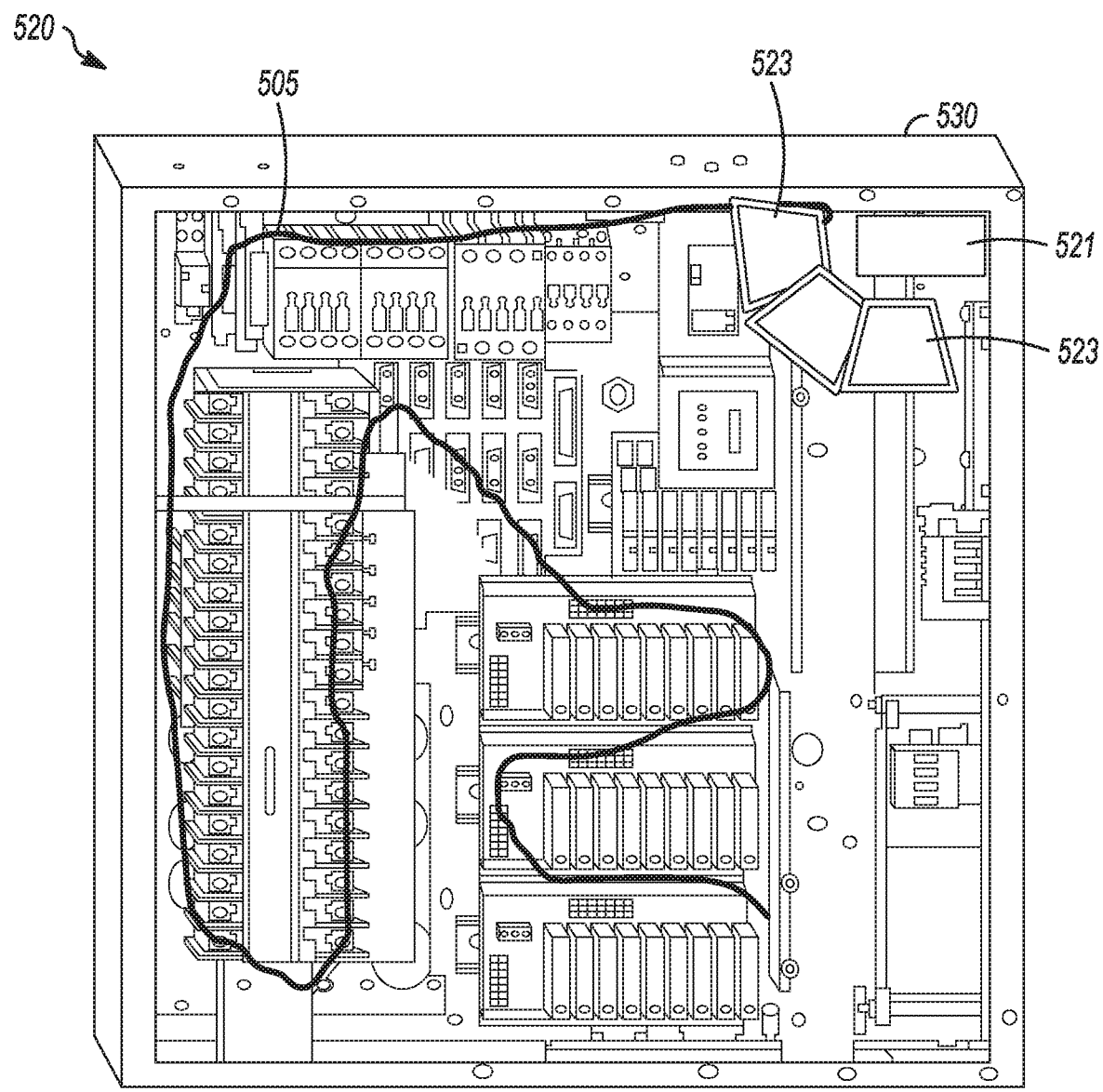
FIG. 5B shows an exemplary embodiment of the linear heat-detection (LHD) cable of FIG. 5A, as well as a number of heat sensors, used within an LPB to detect excessive heat generated within the LPB.

FIG. 5B shows an exemplary embodiment 520 of the linear heat-detection (LHD) cable 505 of FIG. 5A, as well as a number of heat sensors 523, used within an LPB 530 (e.g., a lower LPB) to detect excessive heat generated within the LPB 530. FIG. 5B is also shown to include a control module (CM) 521 located within the LPB 530. Each of the heat sensors 523 may be the same as or similar to the heat sensors 303 of FIG. 3A. Additionally, the CM 521 may be the same as or similar to the CM 301 of FIG. 3A. Although not shown explicitly, in various embodiments the CM 521 may also be coupled to a remote CU or CM outside of the LPB 530. In various embodiments, the heat sensors 523 and the LHD cable 505 are coupled to the CM 521 and/or the remote CU or CM outside the LPB 530.

With continuous reference to both FIGS. 5A and 5B, in various embodiments, the CM 501 of FIG. 5A and the CM 521 of FIG. 5B may be coupled wirelessly to one another (e.g., by wireless operations including radio-frequency, Bluetooth®, and other protocols known in the relevant art or hard-wired (e.g., physically wired directly or through various LAN protocols) to one another. Upon receiving a signal from one or more of the heat sensors 503 and/or the heat sensors 523 indicating that a pre-determined temperature level has been exceeded, one or more of the CM 501, the CM 521, and the remote CU or CM can be pre-programmed to take certain preventive actions, such as shutting down power being delivered to a respective one or both of the LPB 510, 530 or alerting an operator of the tool that an internal temperature level of the LPB 510, 530 has been exceeded. The operator may then perform appropriate actions to safely shut down one or both of the LPB 510, 530.

As noted and described above, one or more of the various embodiments described in detail above may be combined with others of the embodiments. For example, the embodiments of FIGS. 5A and 5B may be combined with the heat sensor 101 of FIGS. 1A and 1B, which is mounted externally to the LPBs 510, 530. In other embodiments, the embodiments of FIGS. 5A and 5B may be combined with both the heat sensor 101 of FIGS. 1A and 1B and the VOC sensor 203 of FIG. 2. In still other embodiments, the embodiments of FIGS. 5A and 5B may be combined with the string of DI-TCs 410, 420 of FIG. 4A. Therefore, various permutations of the embodiments of each of the figures may be combined and include some or all of the various types of heat sensors, string of thermocouples, and heat-detection cable. Such embodiments are considered as being within a scope of the disclosed subject matter.

Consequently, throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Such devices, apparatuses, and methods as described above may be run on various types of devices as described below in more detail. The devices include, for example, a computer or microprocessor, a special-purpose processor, such as a field programmable gate array (FPGA) or an application-specific integrated circuit (ASIC) that is programmed, in software, firmware, or as a hardware implementation, with one or more aspects of the disclosed subject matter described above. At least one of these devices may be included in one of the local control modules, or in one or more remotely-located CMs or CUs.

Moreover, certain embodiments are described herein as including logic or a number of components, modules, or mechanisms. Modules may constitute either software modules (e.g., code embodied on a machine-readable medium or in a transmission signal) or hardware modules. A "hardware module" (e.g., a control module) is a tangible unit capable of performing certain operations and may be configured or arranged in a certain physical manner. In various embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field programmable gate array (FPGA) or an ASIC.

A hardware module may also include programmable logic or circuitry that is temporarily configured by software to perform certain operations. For example, a hardware module may include software encompassed within a general-purpose processor or other programmable processor. It will be appreciated that a decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software may accordingly configure a processor, for example, to constitute a particular hardware-module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods of operation described herein may be at least partially processor-implemented, a processor being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an application program-interface (API)).

The performance of certain of the operations may be distributed among the one or more processors, not only residing within a single machine, but deployed across a number of machines. In some embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

As used herein, the term "or" may be construed in an inclusive or exclusive sense. Further, other embodiments will be understood by a person of ordinary skill in the art upon reading and understanding the disclosure provided. Further, upon reading and understanding the disclosure provided herein, the person of ordinary skill in the art will readily understand that various combinations of the techniques and examples provided herein may all be applied in various combinations.

Although various embodiments are discussed separately, these separate embodiments are not intended to be considered as independent techniques or designs. As indicated above, each of the various portions may be inter-related and each may be used separately or in combination with other embodiments of the heat-detection systems discussed herein. For example, although various embodiments of methods, operations, and processes have been described, these methods, operations, and processes may be used either separately or in various combinations.

Consequently, many modifications and variations can be made, as will be apparent to a person of ordinary skill in the art upon reading and understanding the disclosure provided herein. Functionally equivalent methods and devices within the scope of the disclosure, in addition to those enumerated herein, will be apparent to the skilled artisan from the foregoing descriptions. Portions and features of some embodiments may be included in, or substituted for, those of others. Such modifications and variations are intended to fall within a scope of the appended claims. Therefore, the present disclosure is to be limited only by the terms of the appended claims, along with the full scope of equivalents to which such claims are entitled. It is also to be understood that the terminology used herein is for the purpose of describing particular embodiments only and is not intended to be limiting.

The Abstract of the Disclosure is provided to allow the reader to quickly ascertain the nature of the technical disclosure. The abstract is submitted with the understanding that it will not be used to interpret or limit the claims. In addition, in the foregoing Detailed Description, it may be seen that various features may be grouped together in a single embodiment for the purpose of streamlining the disclosure. This method of disclosure is not to be interpreted as limiting the claims. Thus, the following claims are hereby incorporated into the Detailed Description, with each claim standing on its own as a separate embodiment.

The Following Numbered Examples are Specific Embodiments of the Disclosed Subject Matter Example 1: An embodiment of the disclosed subject matter describes a heat-detection system having at least one heat sensor mounted externally to a local power-box (LPB). The heat sensor has an area-of-detection to detect heat emitted from at least one face of the LPB at one or more locations. A high-absorbance, infrared-collector (HAIC) formed within the LPB is arranged to collect excessive heat generated by a component within the LPB. The excessive heat is correlated to a pre-determined temperature level. A temperature of the collected excessive heat to be measured by the at least one heat sensor. The heat sensors and the HAIC are coupled to a control module.

Example 2: The heat-detection system of Example 1, wherein the HAIC comprises a high-absorptance material to collect radiant energy.

Example 3: The heat-detection system of either Example 1 or Example 2, wherein the HAIC is formed on an interior portion of an external wall of the LPB.

Example 4: The heat-detection system of any one of the preceding Examples, wherein the at least one heat sensor comprises an infrared (IR) sensor.

Example 5: An embodiment of the disclosed subject matter describes a heat-detection system including at least one volatile-organic-compound (VOC) sensor mounted within a device to detect reducing gases produced by outgassing as one or more components within the device approach their respective melting points. The at least one VOC sensor is coupled to a control module.

Example 6: The heat-detection system of Example 5, further comprising one or more fans mounted on the device to form a convection current within the device, the convection current to deliver the reducing gases to the at least one VOC sensor.

Example 7: The heat-detection system of either Example 5 or Example 6, further comprising at least one heat sensor mounted externally to the device, the heat sensor having an area-of-detection to detect heat emitted from at least one face of the device at one or more locations.

Example 8: The heat-detection system of any one of Examples 5 through Example 7, further comprising a high-absorptance, infrared-collector formed within the device configured to collect excessive heat generated by a component within the device, the excessive heat being correlated to a pre-determined temperature level, a temperature of the collected excessive heat to be measured by the at least one heat sensor.

Example 9: The heat-detection system of any one of Examples 5 through Example 8, further comprising a number of heat sensors mounted in the device.

Example 10: An embodiment of the disclosed subject matter describes a heat-detection system for a device. The system includes a number of heat sensors mounted within the device, with each of the heat sensors having an area-of-detection to detect heat emitted from at least one of a plurality of components mounted within the device. A control module is in electrical communication with the number of heat sensors; the control module is arranged to collect electrical signals from the plurality of components where a level of the electrical signals corresponds to a level of temperature. The control module is further arranged to make a determination when at least one of the electrical signals received from the plurality of components exceeds a corresponding pre-determined temperature level.

Example 11: The heat-detection system of Example 10, wherein the control module is further configured to shut down the device based on the determination that the corresponding pre-determined temperature level has been exceeded.

Example 12. The heat-detection system of either Example 10 or Example 11, wherein the control module is further configured to send an alert to an operator of the device based on the determination that the corresponding pre-determined temperature has been exceeded.

Example 13: The heat-detection system of any one of Example 10 through Example 12, further comprising at least one volatile-organic-compound (VOC) sensor mounted within the device to detect reducing gases produced by outgassing as one or more components within the device approach their respective melting points, the at least one VOC sensor being coupled to the control module.

Example 14: The heat-detection system of any one of Example 10 through Example 13, further comprising at least one heat sensor mounted externally to the device, the heat sensor having an area-of-detection to detect heat emitted from at least one face of the device at one or more locations.

Example 15: The heat-detection system of any one of Example 10 through Example 14, further comprising a high-absorptance infrared-collector (HAI C) formed within the device configured to collect excessive heat generated by at least one of the plurality of components within the device, the excessive heat being correlated to a pre-determined temperature level, a temperature of the collected excessive heat to be measured by the at least one heat sensor.

Example 16: An embodiment of the disclosed subject matter describes a heat-detection system to detect heat generated by a device. The system includes at least one rope comprised of a plurality of thermocouples that traverses areas within the device; each of the ropes are arranges to detect heat emitted from at least one of a plurality of components mounted within the device. A control module is in electrical communication with the at least one rope. The control module is arranged to collect electrical signals from the plurality of thermocouples within the at least one rope where a level of the electrical signals corresponds to a level of temperature. The control module is further arranged to make a determination when at least one of the electrical signals received from the plurality of components exceeds a corresponding pre-determined temperature level.

Example 17: The heat-detection system of Example 16, further comprising at least one volatile-organic-compound (VOC) sensor mounted within the device to detect reducing gases produced by outgassing as one or more components within the device approach their respective melting points, the at least one VOC sensor being coupled to the control module.

Example 18: The heat-detection system of either Example 16 or Example 17, further comprising at least one heat sensor mounted externally to the device, the heat sensor having an area-of-detection to detect heat emitted from at least one face of the device at one or more locations.

Example 19: The heat-detection system of any one of Examples 16 through Example 18, further comprising a high-absorptance infrared-collector (HAIC) formed within the device configured to collect excessive heat generated by at least one of the plurality of components within the device, the excessive heat being correlated to a pre-determined temperature level, a temperature of the collected excessive heat to be measured by the at least one heat sensor.

Example 20: An embodiment of the disclosed subject matter describes a heat-detection system to detect heat generated by a device. The system includes at least one linear heat-detection cable placed within the device to detect heat generated in a device. The at least one linear heat-detection cable having a polymer-based thermally reactive sheathing to detect heat emitted from at least one of a plurality of components mounted within the device to detect heat generated by at least one of the plurality of components. A control module is in electrical communication with the at least one linear heat-detection cable with the control module being arranged to collect electrical signals from the at least one linear heat-detection cable. A level of the electrical signals corresponds to a level of temperature. The control module is further arranged to make a determination when at least one of the electrical signals received from the plurality of components exceeds a corresponding pre-determined temperature level.

What is claimed is:

1. A heat-detection system, comprising:
   at least one heat sensor mounted externally to a local power-box (LPB), the heat sensor having an area-of-detection to detect heat emitted from at least one face of the LPB at one or more locations; and
   an infrared-collector (IC) formed within the LPB configured to collect excessive heat generated by a component within the LPB, the excessive heat being correlated to a pre-determined temperature level, a temperature of the collected excessive heat to be measured by the at least one heat sensor, each of the at least one heat sensor and the IC being coupled to a control module.

2. The heat-detection system of claim 1, wherein the IC comprises a high-absorptance material to collect radiant energy.

3. The heat-detection system of claim 1, wherein the IC is formed on an interior portion of an external wall of the LPB.

4. The heat-detection system of claim 1, wherein the at least one heat sensor comprises an infrared (IR) sensor.

* * * * *